United States Patent [19]

Shehadeh

[11] Patent Number: 6,030,622

[45] Date of Patent: Feb. 29, 2000

[54] HERBAL EXTRACT COMPOSITION AND METHOD WITH IMMUNE-BOOSTING CAPABILITY

[76] Inventor: Ahmad Abdallah Shehadeh, 6841 Woodchase Dr., Granite Bay, Calif. 95746

[21] Appl. No.: 09/102,355

[22] Filed: Jun. 23, 1998

[51] Int. Cl.[7] .................................................. A61K 35/78
[52] U.S. Cl. ...................... 424/195.1; 424/439; 426/435; 426/489; 514/885
[58] Field of Search ................................. 424/195.1, 439; 426/435, 489; 514/885

[56] References Cited

U.S. PATENT DOCUMENTS

| | | |
|---|---|---|
| 4,104,373 | 8/1978 | Sichert .................................. 424/195.1 |
| 4,446,130 | 5/1984 | Hachiya et al. . |
| 4,671,959 | 6/1987 | Warren et al. . |
| 4,886,665 | 12/1989 | Kovacs . |
| 5,064,675 | 11/1991 | Jensen et al. . |
| 5,178,865 | 1/1993 | Ho et al. . |
| 5,294,443 | 3/1994 | Lipsky . |
| 5,407,675 | 4/1995 | Etemad-Moghadam . |
| 5,500,340 | 3/1996 | Lipsky . |
| 5,780,086 | 7/1998 | Kirksey et al. ...................... 426/330.3 |

FOREIGN PATENT DOCUMENTS

| | | |
|---|---|---|
| 2286620 | 11/1990 | Japan . |
| 6284872 | 10/1994 | Japan . |

*Primary Examiner*—Leon B. Lankford, Jr.
*Assistant Examiner*—Christopher R. Tate

[57] ABSTRACT

An herbal extract composition comprising extract of ARUM, extract of POMEGRANATE, extract of TEA and extract of HIBISCUS. The herbal extract composition of the invention demonstrates in vitro stimulation of lymphocyte transformation and cytokine production, and in vitro inhibition of gp120 binding, and provides a potential candidate for therapies and treatments for immune disorders and HIV infection.

6 Claims, 3 Drawing Sheets

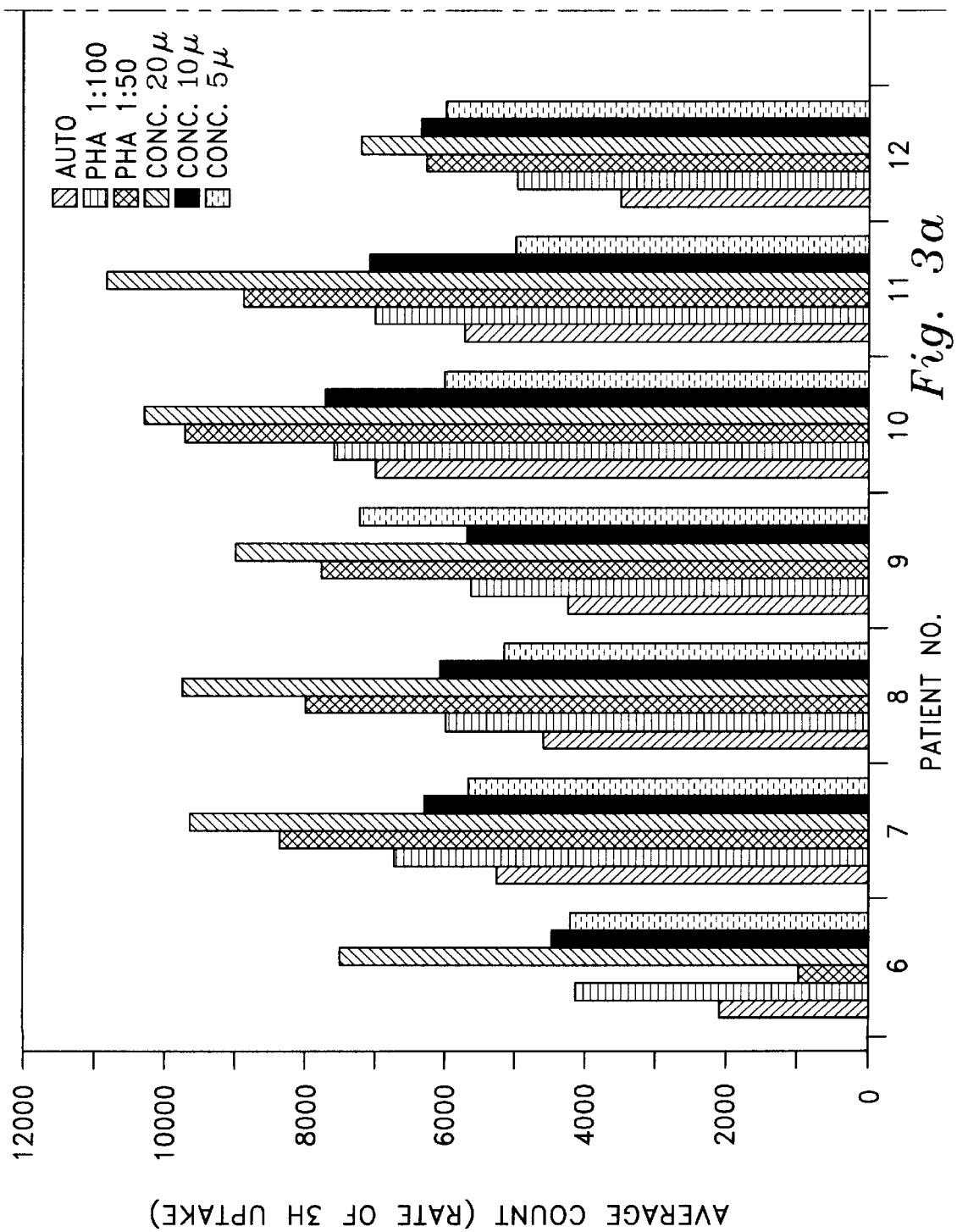

HERBAL EXTRACT COMPOSITION AND METHOD WITH IMMUNE-BOOSTING CAPABILITY

BACKGROUND OF THE INVENTION

1. Field of the Invention

This invention pertains generally to herbal extracts, methods and treatments, and more particularly to a plant-derived or herbal extract composition and method having therapeutic immunity boosting and antiviral effects for boosting or stimulating the natural immune response in humans.

2. Description of the Background Art

The history of herbology is inextricably intertwined with modern medicine. Many familiar modern medications have been developed from ancient healing traditions associated with specific plants. The medicinal properties of many plants have been identified with specific chemical compounds which have been isolated, purified and, in many cases, synthetically reproduced. Many well known drugs were originally derived from plants. Salicylic acid, the precursor for aspirin, was originally isolated from white willow bark and the meadowsweet plant. Quinine, which is used to treat malaria, was derived from Cinchona bark. Vincristine, which is used in cancer treatment, comes from periwinkle. The cancer drug Taxol was originally isolated from the bark and needles of the Pacific Yew Tree. Perhaps most famous are morphine and codeine, which are derived from the opium poppy. Morphine is still the standard against which new synthetic pain relief drugs are measured.

The use of plants for medicinal purposes predates recorded history. Marshmallow root, hyacinth and yarrow have been found carefully placed around the bones of a stone age man in Iraq. Marshmallow root is a demulcent herb with anti-inflammatory properties, and is used to treat inflamed or irritated mucous membranes. Hyacinth is used as a diuretic to encourage tissues to give up excess water. Yarrow is a time honored cold and fever remedy which may once have been used as widely as aspirin is today.

Modern physicians, particularly in the United States, tend to rely on treatments using synthetic or chemically manufactured drugs. Rather than using whole plants or plant extracts for treatment, pharmacologists tend to identify, isolate, extract and synthesize the active compounds from plants for use in treatment. This approach, however, has drawbacks. In addition to individual physiologically active compounds present in a plant, there are also minerals, vitamins, glycosides, oils, alkaloids, bioflavinoids, and other substances which can be important in supporting the medicinal properties of a particular plant. These additional substances can provide a synergistic effect which is absent when purified or synthetic physiologically active compounds are used alone. Additionally, the toxicity of purified physiologically active compounds is generally higher than when the physiologically active compounds are present with the other plant substances.

The efficacy of various herbal remedies, extracts, potions and treatments is well known, and therapeutic herb products are increasingly recognized as desirable alternatives to synthetic drugs. For example, U.S. Pat. No. 4,446,130 discloses the use of a ginseng extract having stimulative and diurectic effects. U.S. Pat. No. 4,886,665 teaches the use of a pharmaceutical preparation of oats and nettle extracts. U.S. Pat. No. 4,671,959 discloses the use of mixtures of natural oils for stress reduction. U.S. Pat. No. 5,064,675 relates an herbal extract composition which provides a calming effect. U.S. Pat. No. 5,407,675 discloses an herbal extract used for scalp treatment. U.S. Pat. No. 5,178,865 discloses an herbal extract mix which inhibits infection of human immunodeficiency virus or HIV in vitro. U.S. Pat. No. 5,500,340 and U.S. Pat. No. 5,294,443 disclose the use of herbal extracts for immunosuppression and treatment of autoimmune disorders.

The human immune response is extremely complex and requires constant interaction by the cells involved in the immune system. Intracellular communication is facilitated by secretion of chemical messenger proteins known as cytokines, which act by enhancing cell growth, promoting cell activation, directing cellular traffic, stimulating macrophage function, destroying antigens, and other functions. Cytokines generally comprise lymphokines, which are secreted by T-lymphocytes, and monokines secreted by monocytes. Interferons, which are used to defend against viral infection and tumor cell growth, are an important class of cytokines. Cytokines also include interleukins, which are involved in cell differentiation, and tumor necrosis factors and transforming growth factors which are involved in mediating inflammation and cytotoxic reactions. Another important set of proteins in the human immune response are the immunoglobulins, which are secreted by B lymphocytes. Immunoglobulins serve as antibodies which counter viral, bacterial and other antigens.

Persons who suffer from immuno-suppressive diseases or conditions such as human immunodeficiency virus (HIV), cancer, hepatitis, renal failure, diabetes, asthma, arthritis, and the like often experience decreased levels of lymphocytes and correspondingly decreased levels of cytokines. For example, where individuals have been infected by HIV, lymphocytes having a cell surface antigen known as CD4 are present in uncharacteristically low numbers. While in healthy individuals these CD4 lymphocyte cells are present in concentrations of about 800 cells per milliliter of serum, HIV-infected individuals exhibit as few as 200 CD4 cells per milliliter of serum when opportunistic infections develop. Specific types of CD4 lymphocytes known as TH1 and TH2 cells appear to be particularly important in the cell-mediated response to HIV infection. TH1 cells produce interleukin-2 (IL-2) and gamma interferon (IFNγ). TH2 cells produce interleukins -4, -5 and -10 (IL-4, IL-5 and IL-10). The cytokines secreted by TH1 and TH2 cells are believed to have an opposing effect on each other, with cytokines secreted by TH1 cells acting to regulate the cytokine production of TH2 cells, and vice versa. Early in the course of HIV infection, the TH1 response dominates, and secretion of IL-2 by TH1 cells increases the activity of CD8 lymphocytes.

The naturally occurring interferons, interleukins and immunoglobulins secreted by lymphocytes are well engineered for regulating the human immune response, and treatment of immunodeficient or immuno-suppressed patients with interferons, interleukins and immunoglobulins can be effective. Industrial production of interferons, interleukins and immunoglobulins via genetic engineering techniques is well known, wherein the genes responsible for producing these proteins are introduced into bacteria, which are then grown and harvested. The interferons, interleukins and immunoglobulins secreted by the genetically modified bacteria are then purified and delivered to patients by syringe or intravenous methods. An oral delivery method for providing interferons, interleukins and immunoglobulins to patients has not yet been realized, as stomach acids and enzymes tend to break down these proteins before they can be delivered to the bloodstream.

Various herbs are believed to have a beneficial effect on the human immune system. For example, *Echinacea Pur-*

*purea* and *Echinacea Angustifolia* are believed to stimulate T-cell activity. Mowery, D. B.; *The Scientific Validation of Herbal Medicine*, Keats Publishing, Inc., New Canaan Press, 1986. P. 118–119. *Astragulas Membranaceous* is believed to be able to stimulate production of interferon and Immunoglobulins A and G (IgA and IgG) in mice. Kaiser, J. D.; *Immune Power. A Comprehensive Treatment Program for HIV*. St. Martin's Press, New York, 1993, p. 59–60. However, a plant-derived or herbal extract which effectively provides a stimulative or boosting effect to the human immune system has heretofore been unknown.

Accordingly, there is a need for an herbal extract composition and method composition and method which provides a health supplement and for treatment generally persons or animals having diseases or conditions which suppress the immune response. The present invention satisfies these needs, as well as others, and generally overcomes the deficiencies found in the background art.

SUMMARY OF THE INVENTION

The present invention is an herbal extract composition and method of making and using the same for stimulating or boosting the immune response in humans and animals. The names, classifications, and geographic origins of the plants or herbs used with the invention are provided below in Table 1.

TABLE 1

| Plant Name | Classification | Origin | Part(s) Used |
|---|---|---|---|
| Arum | Araceae | Asia, Africa, Europe, Americas | Leaf & Or Root |
| Pomegranate | Punica, Granatum/of Punicaceae family | Syria, Iraq, Turkey, Italy, and other parts of the world | Fruit Peels |
| Hibiscus | Mallow Family, Malvaceae | Africa, East Indies, and China | Flowers |
| Tea | Camelia Sinensis of the Family Theaceae, the tea family | China, Japan, East Indies | Leaf |

Typically, the fresh or dried leaves, seeds, bark, fruit, peel, flowers and/or roots of each of the above plants or herbs or other plants and herbs from the above families may be used in preparation of the herbal extract composition of the invention as described in detail below. However, the preferred plants or herbs and the preferred portions of ARUM, POMEGRANATE, TEA and HIBISCUS used for extraction are as shown in Table 1. Generally the herbs are extracted with hot water, although aqueous ethanolic solutions and ethanol may alternatively be used for extraction.

In general terms, the herbal extract composition of the invention comprises of extract of ARUM. Another embodiment of the invention is an herbal extract composition which comprises of between approximately ten percent and approximately ninety percent extract of ARUM, and between approximately ten percent and approximately ninety percent extract of POMEGRANATE. The herbal extract composition of the invention may further comprise of between approximately ten percent and approximately ninety percent extract of TEA, and/or between approximately ten percent and approximately ninety percent extract of HIBISCUS. Preferably, the herbal extract composition of the invention comprises of generally equal portions of extract of ARUM, extract of POMEGRANATE, extract of TEA and extract of HIBISCUS.

The herbal extract composition of the invention provides a healthy and nutritious supplement to the human diet in that it contains Vitamin C, Vitamin E, Vitamin D2, Vitamin D3, Vitamin K, solubilized minerals including phosphorus, sodium, potassium, zinc, magnesium and copper, and numerous beneficial proteins. The proteins include various cytokine or cytokine-like proteins, and immunoglobulin or immunoglobulin-like proteins, which are believed to provide a stimulating or boosting effect to the immune system. As a nutrition supplement the herbal extract composition of the invention is ingested orally, or may be applied topically.

Experimental results (discussed below) indicate that the herbal extract composition of the invention is effective in boosting the human immune response. In vitro experiments show that the herbal extract composition of the invention stimulates cell mediated immunity by stimulating blastogenesis or blast transformation of lymphocytes and by stimulating cytokine production in lymphocyte suspensions from normal persons, from leukemia patients, and from patients suffering from renal failure. Initial experimental results also indicate that the herbal extract composition of the invention is effective at inhibiting HIV infection in vitro. These experiments and the resulting data demonstrate that the herbal extract composition of the invention is a useful source or candidate for potential immune disorder therapies.

The method of making the herbal extract composition of the invention preferably comprises the steps of preparing an extract of ARUM, preparing and extract of POMEGRANATE, preparing and extract of TEA, preparing an extract of HIBISCUS, and combining the extracts of ARUM, POMEGRANATE, TEA and HIBISCUS.

The method of using the invention for stimulating in vitro cell mediated immunity comprises contacting or exposing cells to an efficacious amount of a preparation consisting essentially of extract of ARUM, extract of POMEGRANATE, extract of TEA and extract of HIBISCUS.

The method of using the invention for stimulating in vitro lymphocyte blastogenesis comprises contacting or exposing lymphocyte suspensions to an efficacious amount of a preparation consisting essentially of extract of ARUM, extract of POMEGRANATE, extract of TEA and extract of HIBISCUS.

The method of using the invention for stimulating in vitro cytokine production in peripheral mononuclear blood cells comprises contacting or exposing such cells to an efficacious amount of a preparation consisting essentially of extract of ARUM, extract of POMEGRANATE, extract of TEA and extract of HIBISCUS.

An object of the invention is to provide an herbal extract composition and method which is a useful source or candidate for therapies and treatments for humans and animals suffering from immunosuppressive and auto-immune diseases, disorders, infections or conditions.

Another object of the invention is to provide an herbal extract composition and method which provides a nutritious dietary supplement for humans and animals.

Another object of the invention is to provide an herbal extract composition and method which stimulates or boosts the immune response in humans and animals.

Another object of the invention is to provide an herbal extract composition and method which stimulates in vitro cell mediated immunity.

Another object of the invention is to provide an herbal extract composition and method which stimulates cell mediated immunity in humans and animals.

Another object of the invention is to provide an herbal extract composition and method which stimulates in vitro blast transformation or blastogenesis of lymphocytes.

Another object of the invention is to provide an herbal extract composition and method which stimulates blast transformation or blastogenesis of lymphocytes in humans and animals.

Another object of the invention is to provide an herbal extract composition and method which stimulates in vitro cytokine production in peripheral mononuclear blood cells.

Another object of the invention is to provide an herbal extract composition and method which stimulates cytokine production in humans and animals.

Another object of the invention is to provide an herbal extract composition and method for in vitro inhibition of gp120 binding to MT-4 cells.

Another object of the invention is to provide an herbal extract composition and method for in vitro inhibition of HIV infection of MT-4 cells. extract composition comprising extract of ARUM, extract of POMEGRANATE, extract of TEA and extract of HIBISCUS for inhibiting HIV infection in humans.

Another object of the invention is to provide an herbal extract composition and method for treating immunosuppresive disorders and conditions which is relatively nontoxic.

Another object of the invention is to provide an herbal extract composition which includes various cytokine and/or cytokine-like proteins, and immunoglobulin and/or immunoglobulin-like proteins.

Another object of the invention is to provide an herbal extract composition that contains Vitamin C, Vitamin E, Vitamin D2, Vitamin D3, Vitamin K, solubilized minerals including phosphorus, sodium, potassium, zinc, magnesium and copper, and numerous beneficial proteins.

Further objects and advantages of the invention will be brought out in the following portions of the specification, wherein the detailed description is for the purpose of fully disclosing the preferred embodiment of the invention without placing limitations thereon.

BRIEF DESCRIPTION OF THE DRAWINGS

The present invention will be more fully understood by reference to the following drawings, which are for illustrative purposes only.

DETAILED DESCRIPTION OF THE PREFERRED EMBODIMENTS

Figure 2:
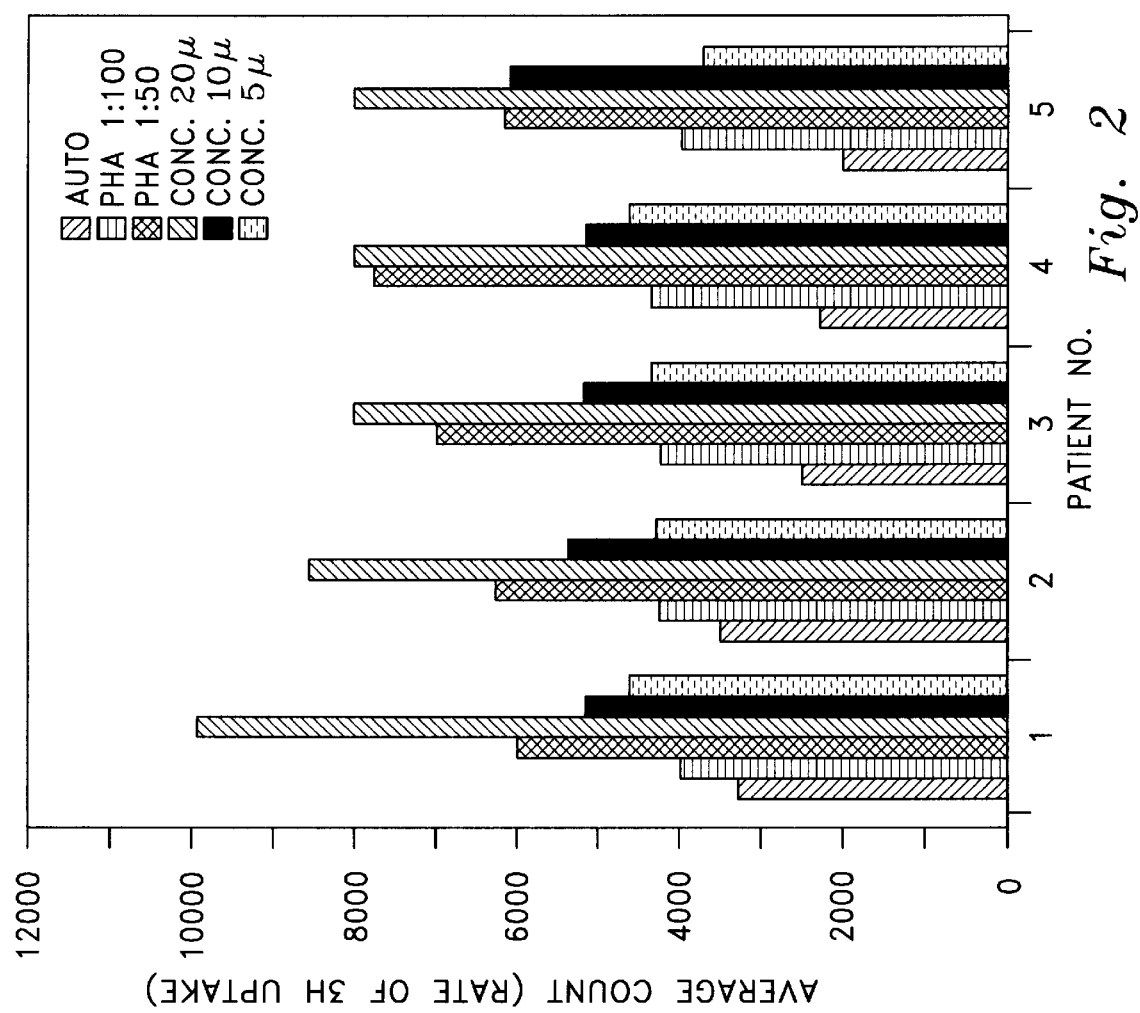
FIG. 2 is a graphic representation of the effect of the herbal extract of the invention on blastogenesis of lymphocytes from leukemia patients.

The present invention pertains generally to the use of herbal extracts of ARUM, POMEGRANATE, TEA and HIBISCUS, and various combinations thereof for boosting or stimulating the immune response in humans and animals, for treatment of persons and animals suffering from immunosuppressive and auto-immune diseases or conditions, and for inhibiting HIV infection in humans.

Example 1 illustrates the process of preparation and composition of herbal extracts of ARUM, POMEGRANATE, TEA and HIBISCUS. Example 2 relates the use of an herbal extract composition comprising extract of ARUM, extract of POMEGRANATE, extract of TEA and extract of HIBISCUS for in vitro blast transformation of normal lymphocyte suspensions. Example 3 relates the use of the herbal extract composition comprising extract of ARUM, extract of POMEGRANATE, extract of TEA and extract of HIBISCUS for in vitro blastogenesis of peripheral blood lymphocytes from patients with acute leukemia. Example 4 relates the use of the herbal extract composition comprising extract of ARUM, extract of POMEGRANATE, extract of TEA and extract of HIBISCUS for in vitro blastogenesis of peripheral blood lymphocytes from patients with renal failure. Example 5 relates the use of the herbal extract composition comprising extract of ARUM, extract of POMEGRANATE, extract of TEA and extract of HIBISCUS for in vitro stimulation of cytokine production in peripheral blood mononuclear cells (PMBC) from normal patients. Example 6 describes the use of the herbal extract composition comprising extract of ARUM, extract of POMEGRANATE, extract of TEA and extract of HIBISCUS for in vitro inhibition of gp120 binding to MT-4 cells as measured with OKT-4A mAb binding. Example 7 describes the use of the herbal extract composition comprising extract of ARUM, extract of POMEGRANATE, extract of TEA and extract of HIBISCUS for in vitro inhibition of gp120 binding to MT-4 cells as measured with anti gp120 mAb. Example 8 describes the analytical examination of combined extracts of ARUM, POMEGRANATE, TEA and HIBISCUS.

EXAMPLE 1

Extract Preparation

This Example describes the preparation and combination of extracts of ARUM, POMEGRANATE, TEA and HIBISCUS. Reference is made to Table 1 above as to the preferred plant parts of ARUM, POMEGRANATE, TEA and HIBISCUS used for the extraction processes. The processes described below can be scaled up to produce larger quantities of extracts. The details provided for preparation of the following abstracts reflect the presently preferred method for extract preparations and should not be considered as limiting. The quantities and times described below can be varied substantially to provide suitable extracts of ARUM, POMEGRANATE, TEA and HIBISCUS in accordance with the invention.

1. Preparation of Extract of ARUM.

Approximately 20 grams of dried, finely crushed ARUM and one liter of distilled water were added to a stainless steel pressure cooker vessel and sealed therein with stainless steel lid. The mix therein was heated to boiling (approximately 100° C.) and allowed to boil for approximately forty five minutes, and was then heated to approximately 130° C. and boiled for approximately 15 minutes, then allowed to cool below 100° C. to provide a liquid extract of ARUM. The extract of ARUM was used while still warm or hot in the manner described below.

2. Preparation of Extract of POMEGRANATE.

Approximately 60 grams of dried, finely crushed POMEGRANATE and one liter of distilled water were added to a stainless steel pressure cooker vessel and sealed therein with stainless steel lid. The mix therein was heated to boiling (approximately 100° C.) and allowed to boil for approximately forty five minutes, and was then heated to approximately 130° C. and boiled for approximately 15 minutes, then allowed to cool below 100° C. to provide a liquid extract of POMEGRANATE. The extract of POMEGRANATE was used while still warm or hot in the manner described below.

3. Preparation of Extract of TEA.

Approximately 15 grams of dried, finely crushed TEA and one liter of distilled water were added to a stainless steel pressure cooker vessel and sealed therein with stainless steel lid. The mix therein was heated to boiling (approximately 100° C.) and allowed to boil for approximately forty five minutes, and was then heated to approximately 130° C. and boiled for approximately 15 minutes, then allowed to cool below 100° C. to provide a liquid extract of TEA. The extract of TEA was used while still warm or hot in the manner described below.

4. Preparation of Extract of HIBISCUS.

Approximately 40 grams of dried, finely crushed HIBISCUS and one liter of distilled water were added to a stainless steel pressure cooker vessel and sealed therein with stainless steel lid. The mix therein was heated to boiling (approximately 100° C.) and allowed to boil for approximately forty five minutes, and was then heated to approximately 130° C. and boiled for approximately 15 minutes, then allowed to cool below 100° C. to provide a liquid extract of HIBISCUS. The extract of HIBISCUS was used while still warm or hot in the manner described below vessel.

5. Preparation of Combined Extracts of ARUM and POMEGRANATE

Approximately 50 ml of each of extract of ARUM and extract of POMEGRANATE were transferred while still warm to hot (between approximately 40° C. and 100° C.) to a stainless steel pressure cooker vessel and sealed therein with stainless steel lid, and heated together, with continuous mixing or agitation, for approximately 1.5 hours at approximately 100° C. The mix thus obtained can be cooled and then stored under refrigeration, or used while still warm to hot as described below to prepare further extract combinations. Combined extracts of ARUM and TEA, ARUM and HIBISCUS, POMEGRANATE and TEA, and POMEGRANATE and HIBISCUS were also prepared by a generally identical procedure.

6. Preparation of Combined Extracts of ARUM, POMEGRANATE, TEA and HIBISCUS

Approximately 100 ml of combined extracts of ARUM and POMEGRANATE as prepared above, together with approximately 50 ml each of extract of TEA as prepared above, and approximately 50 ml of extract of HIBISCUS as prepared above, were transferred while still warm to hot (between approximately 40° C. and 100° C.) to a stainless steel pressure cooker vessel and sealed therein with stainless steel lid, and heated together, with continuous mixing or agitation, for approximately 1.5 hours at approximately 100° C. The mix thus obtained has generally equal portions of each of the extracts of ARUM, POMEGRANATE, TEA and HIBISCUS described above. The combined mix of extracts of ARUM, POMEGRANATE, TEA and HIBISCUS was allowed to cool to room temperature. During cooling, buffer solution ($Na_2HPO_4/NaH_2PO_4$) was added to the combined mix while the mix is at approximately 30° C. to 60° C., to provide a slightly acidic pH to the mix. Preferably, the pH of the combined extracts is adjusted to approximately 4.0, and more preferably to approximately 3.8, although providing a pH below 7 is suitable. Following the above procedure, the combined extracts of ARUM, POMEGRANATE, TEA and HIBISCUS were stored under refrigeration at approximately 4° C. A trace of Sodium benzoate may be added to the combined extracts as a preservative, and flavoring or food colorants may be added if desired.

The chemical analysis results for the combined mix of extracts of ARUM, POMEGRANATE, TEA, HIBISCUS is described below under Example 8.

The above procedure was used to prepare a combined mix of extracts of ARUM, POMEGRANATE and TEA by omitting the extract of HIBISCUS. The above procedure was also used to prepare a combined mix of extracts of ARUM, POMEGRANATE and HIBISCUS by omitting the extract of TEA. The above procedure was further used to prepare combined mix of extracts of POMEGRANATE, TEA and HIBISCUS by omitting the extract of ARUM. The above procedure was further used to prepare the combined mix of extracts of POMEGRANATE and TEA by omitting the extracts of ARUM and HIBISCUS.

EXAMPLE 2

In Vitro Blast Transformation of Lymphocytes From Normal Patients

This Example describes the effect of the herbal extract composition comprising extract of ARUM, extract of POMEGRANATE, extract of TEA and extract of HIBISCUS described in Example 1 on cell mediated immunity, which was measured by in vitro blast transformation or blastogenesis of normal lymphocytes.

Blastogenesis is the initial step in the induction of cell mediated immunity, and is associated with the release or secretion of various interleukins which are essential for intercellular interaction of the immune system. Cell mediated immunity is involved with the human body's defense against malignancies, certain viral infections including HIV, intercellular bacterial infection, as well as regulation of different cellular and humoral immunological interactions and prevention of autoimmune reactions.

Blast transformation was measured via a conventional lymphocyte stimulation test wherein $^3H$ (tritiated) thymidine is added to lymphocyte suspensions, followed by incubation, cell harvesting and measuring radioactivity of the harvested cells. A high radioactivity count indicates that the lymphocytes have undergone transformation and taken up the $^3H$ thymidine.

Lymphocytes from the whole blood of three normal patients were obtained by density gradient separation on Ficoll Isopaque. Multi-well microtiter plates were prepared containing lymphocyte suspensions in Hanks solution supplemented with 10% fetal calf serum, penicillin and streptomycin. 5 $\mu l$, 10 $\mu l$ and 20 $\mu l$ of the combined mix of extracts of ARUM, POMEGRANATE, TEA, HIBISCUS were added to wells on each of the plates. The final volume of lymphocyte suspension in each well was 0.2 ml. The microtiter plates were then incubated for 72 hours at 37° C. in a $CO_2$ incubator. To each well 0.05 ml of $^3H$ (tritiated) thymidine was then added, followed by a further 24 hours of incubation at 37° C., after which the wells were harvested with an automatic multiple harvester, and radioactivity was measured with a scintillation counter. A stimulation index was calculated from the average counts for each concentration of combined extract. The results are shown in Table 2 and FIG. 1.

TABLE 2

|  | Average Counts (Rate of $^3H$ Uptake) | Stimulation Index |
| --- | --- | --- |
| No Combined Extracts | 284 Counts/Min (Background) | 0 |
| 20 $\mu l$ Combined Extracts | 815 Counts/Min | 2.86 |
| 10 $\mu l$ Combined Extracts | 723 Counts/Min | 2.54 |
| 5 $\mu l$ Combined Extracts | 463 Counts/Min | 1.63 |

Figure 1:
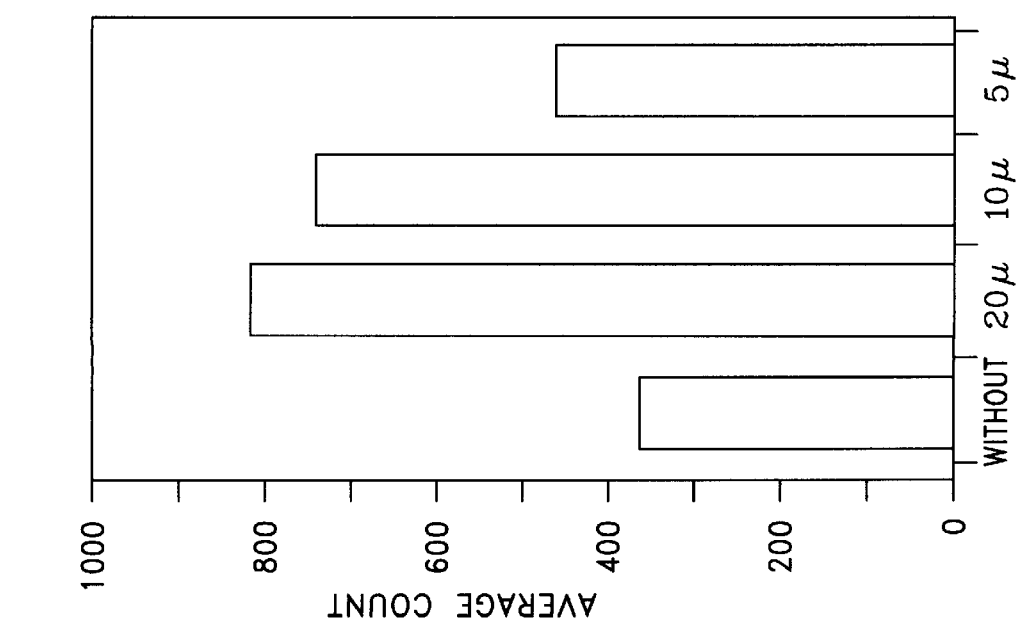
FIG. 1 is a graphic representation of the effect of the herbal extract composition of the invention on blastogenesis of normal lymphocytes.

The results illustrated in Table 2 and FIG. 1 show that addition of increasing quantities of the combined extracts to lymphocyte suspensions results in increasing amounts or degrees of lymphocyte transformation or blastogenesis, as shown by increased radiation counts due to increased $^3$H uptake. These results indicate that the herbal extract composition comprising extract of ARUM, extract of POMEGRANATE, extract of TEA and extract of HIBISCUS boost or stimulate cell mediated immunity by stimulating blastogenesis and the resulting secretion of cytokines in normal persons. These results further demonstrate that the herbal extract composition of the invention is a useful source or candidate for potential immune disorder therapies and treatments.

EXAMPLE 3

In Vitro Blastogenesis of Peripheral Blood Lymphocytes from Patients With Acute Leukemia This Example describes the effect of the herbal extract composition comprising extract of ARUM, extract of POMEGRANATE, extract of TEA and extract of HIBISCUS described in Example 1 on cell mediated immunity, which was further measured by in vitro blast transformation or blastogenesis of lymphocytes from five leukemia patients. PHA (phytohaemagglutinin), a known powerful mitogen which stimulates lymphocyte transformation, was used as a control to gauge or measure the efficacy of the combined extracts.

Multi-well microtiter plates were prepared containing lymphocyte suspensions from five leukemia patients in Hanks solution supplemented with 10% fetal calf serum, penicillin and streptomycin. Five μl, 10 μl and 20 μl amounts of the combined mix of extracts of ARUM, POMEGRANATE, TEA, HIBISCUS were added to wells on each of the plates. Additionally, PHA (Phytohaemagglutinin) in concentrations of 1:50 and 1:100 were added to wells as controls. The final volume of lymphocyte suspension in each well was 0.2 ml. The microtiter plates were incubated for 72 hours at 37° C. in a $CO_2$ incubator, after which 0.05 ml of $^3$H (tritiated) thymidine was then added to each well, followed by a further 24 hours of incubation at 37° C. The wells were harvested with an automatic multiple harvester, and radioactivity was measured with a scintillation counter, and a stimulation index was calculated for each concentration of combined extracts. The results are shown in Table 3 and FIG. 2.

TABLE 3

| Patient No. | Counts Auto (Control) | Counts PHA 1:100 | Counts PHA 1:50 | Counts (St. Index) 20 μl Extracts | Counts (St. Index) 10 μl Extracts | Counts (St. Index) 5 μl Extracts |
|---|---|---|---|---|---|---|
| 1 | 3236 | 3997 | 5949 | 9890 (3.0) | 5179 (1.6) | 4680 (1.14) |
| 2 | 3462 | 4297 | 6288 | 8365 (2.4) | 5340 (1.5) | 4100 (1.18) |
| 3 | 2384 | 4239 | 6857 | 7850 (3.2) | 5100 (2.1) | 4390 (1.8) |
| 4 | 2222 | 4339 | 7600 | 7750 (4.48) | 5060 (2.27) | 4600 (2.07) |
| 5 | 1890 | 3960 | 6010 | 7800 (4.1) | 5960 (3.15) | 3680 (1.94) |

The results illustrated in Table 3 and FIG. 2 show that addition of increasing quantities of the combined extracts to lymphocyte suspensions from leukemia patients results in increasing amounts of lymphocyte transformation or blastogenesis, as shown by increased radiation counts due to increased $^3$H uptake. The herbal extract composition comprising extract of ARUM, extract of POMEGRANATE, extract of TEA and extract of HIBISCUS exhibits an ability to stimulate lymphocyte transformation which is at least as great as PHA. Blast transformation stimulation is increased by 306% at the highest (20 μl) concentration. These results indicate that the herbal extract composition comprising extract of ARUM, extract of POMEGRANATE, extract of TEA and extract of HIBISCUS boosts or stimulates cell mediated immunity in vitro by stimulating lymphocyte blastogenesis, and thus the resulting secretion of cytokines, in lymphocytes from patients suffering from leukemia. These results further demonstrate that the herbal extract composition of the invention is a useful source or candidate for potential immune disorder therapies and treatments.

EXAMPLE 4

In Vitro Blastogenesis of Peripheral Blood Lymphocytes from Patients With Renal Failure This Example describes the effect of the herbal extract composition comprising extract of ARUM, extract of POMEGRANATE, extract of TEA and extract of HIBISCUS described in Example 1 on cell mediated immunity, which was further measured by in vitro blast transformation or blastogenesis of lymphocytes from fifteen patients suffering from renal failure. PHA (phytohaemagglutinin) in two concentrations was used as a control to gauge or measure the efficacy of the combined extracts.

Multi-well microtiter plates were prepared containing lymphocyte suspensions from five leukemia patients in Hanks solution supplemented with 10% fetal calf serum, penicillin and streptomycin. The combined mix of extracts of ARUM, POMEGRANATE, TEA, HIBISCUS was added to wells on each of the plates in 5 μl, 10 μl and 20 μl amounts. PHA in concentrations of 1:50 and 1:100 were added to wells as controls. The final volume of lymphocyte suspension in each well was 0.2 ml. The microtiter plates were incubated for 72 hours at 37° C. in a $CO_2$ incubator, after which 0.05 ml of $^3$H (tritiated) thymidine was then added to each well, followed by a further 24 hours of incubation at 37° C. The wells were harvested with an automatic multiple harvester, and radioactivity was measured with a scintillation counter, and a stimulation index was calculated for each concentration of combined extracts. The results are shown in Table 4 and FIG. 3.

TABLE 4

| Patient No. | Counts Auto (Control) | Counts PHA 1:100 | Counts PHA 1:50 | Counts (St. Index) 20 μl Extracts | Counts (St. Index) 10 μl Extracts | Counts (St. Index) 5 μl Extracts |
|---|---|---|---|---|---|---|
| 6 | 2050 | 4150 | 5090 | 7650 (3.7) | 4535 (2.2) | 4290 (2.09) |
| 7 | 5232 | 6718 | 8350 | 9460 (1.81) | 6240 (1.19) | 5640 (1.08) |
| 8 | 4643 | 5950 | 7980 | 9680 (2.08) | 5980 (1.29) | 5100 (1.10) |
| 9 | 4150 | 5660 | 7790 | 8940 (2.15) | 5710 (1.37) | 5200 (1.25) |
| 10 | 6939 | 7600 | 9800 | 10250 (1.4) | 7800 (1.12) | 7100 (1.02) |
| 11 | 5765 | 6830 | 8910 | 10630 (1.8) | 6920 (1.2) | 5940 (1.03) |
| 12 | 4531 | 5100 | 6030 | 7150 (1.57) | 6120 (1.35) | 5090 (1.12) |
| 13 | 5920 | 5700 | 7080 | 7980 (1.30) | 7030 | 5850 (0.9) |
| 14 | 6203 | 6800 | 7503 | 8250 (1.30) | 7105 | 6930 (0.89) |
| 15 | 4539 | 5240 | 6015 | 7030 (1.548) | 6090 | 5440 (1.19) |

TABLE 4-continued

| Patient No. | Counts Auto (Control) | Counts PHA 1:100 | Counts PHA 1:50 | Counts (St. Index) 20 µl Extracts | Counts (St. Index) 10 µl Extracts | Counts (St. Index) 5 µl Extracts |
|---|---|---|---|---|---|---|
| 16 | 4605 | 5405 | 6250 | 7654 (1.66) | 6320 | 5660 (1.229) |
| 17 | 3260 | 4100 | 5209 | 6800 (2.805) | 5400 | 4300 (1.319) |
| 18 | 4620 | 5410 | 6430 | 7930 (1.71) | 6250 | 5430 (1.175) |
| 19 | 4330 | 5310 | 6100 | 7800 (1.801) | 6050 | 5450 (1.25) |
| 20 | 3236 | 4100 | 5260 | 7260 (2.24) | 5380 | 4330 (1.338) |

Figure 3B:
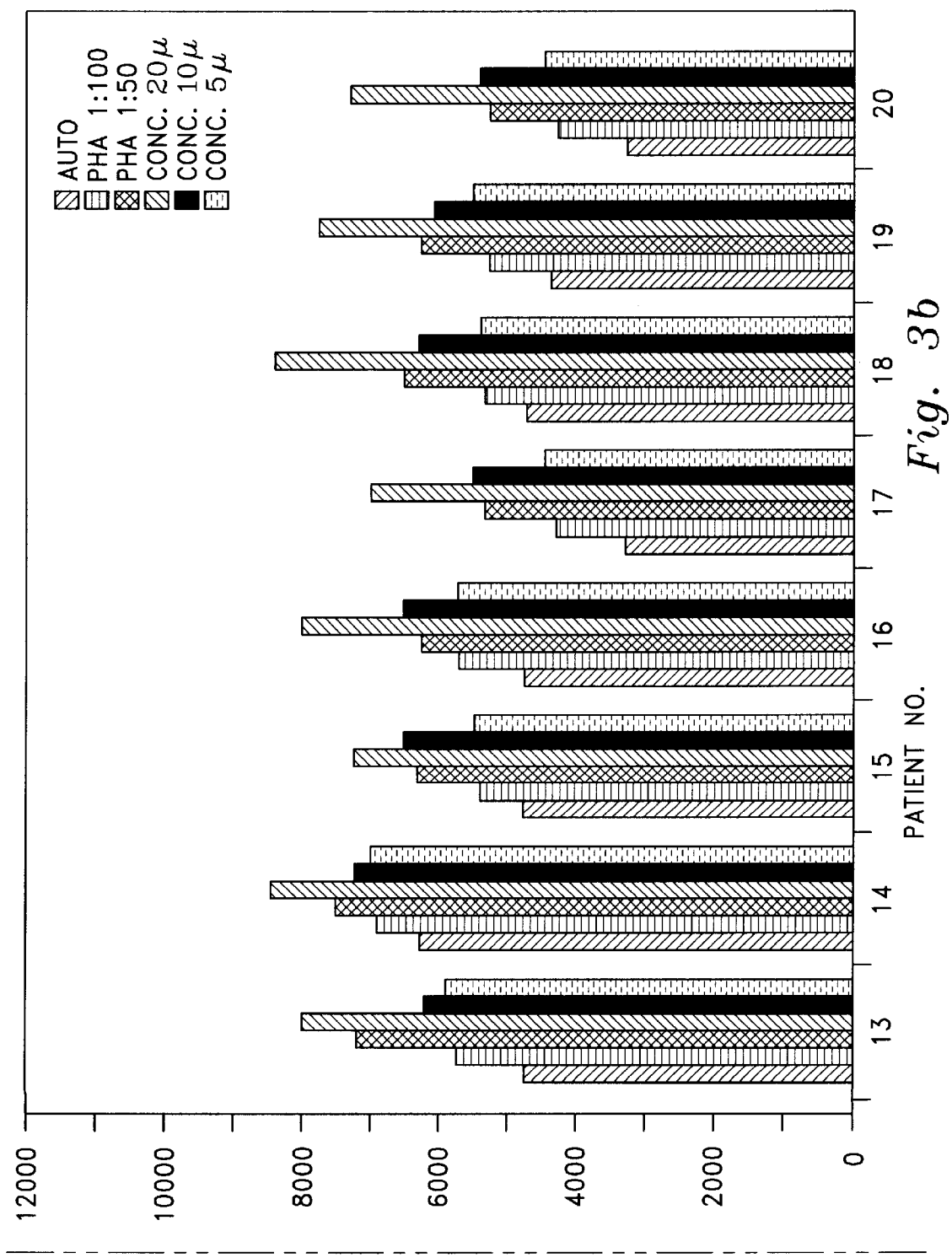
FIG. 3 is a graphic representation of the effect of the herbal extract of the invention on blastogenesis of lymphocytes from patients having renal failure.

The results illustrated in Table 4 and FIG. 3 show that addition of increasing quantities of the combined extracts to lymphocyte suspensions from renal failure patients results in increasing amounts of lymphocyte transformation or blastogenesis, as shown by increased radiation counts due to increased $^3$H Uptake. The combined extracts of ARUM, POMEGRANATE, TEA and HIBISCUS exhibit an ability to stimulate lymphocyte transformation which is at least as great as PHA. Blast transformation stimulation is increased by 306% at the highest (20 µl) concentration. These results indicate that the combined extracts of ARUM, POMEGRANATE, TEA and HIBISCUS boost or stimulate cell mediated immunity in vitro by stimulating lymphocyte blastogenesis and the resulting secretion of cytokines in lymphocytes from patients suffering from renal failure. These results further demonstrate that the herbal extract composition of the invention is a useful source or candidate for potential immune disorder therapies and treatments.

EXAMPLE 5

Stimulation of Cytokine Production in Normal Persons

The effect of the herbal extract composition comprising extract of ARUM, extract of POMEGRANATE, extract of TEA and extract of HIBISCUS on cytokine production by human peripheral mononuclear blood cells (PMBC) was measured using the method described by D. Schols and E. De Clencq in *Human Immunodeficiency Virus Type gp120 Induces Anergy In Human Peripheral Blood Lymphocytes By Inducing Interleukin Production*, J. Virol. Vol. 70, p. 4953–4960 (1996), the contents of which are incorporated herein by reference. The average results for two normal patients are shown in Table 5.

TABLE 5

| | % Combined Extracts | IL-2 pg/ml | IL-4 pg/ml | IL-10 pg/ml | IFN-γ pg/ml |
|---|---|---|---|---|---|
| Medium | 0% | < | ND | 35 | 31 |
| | 10% | 48 | ND | 502 | 197 |
| | 1% | < | ND | 653 | < |
| | 0.1% | < | ND | 232 | < |
| PHA 2 µg/ml | 0% | 541 | ND | 178 | 969 |
| | 10% | 1221 | ND | 471 | 926 |
| | 1% | 585 | ND | 224 | 969 |
| | 0.1% | 524 | ND | 203 | 740 |
| α-CD3 1/1000 | 0% | 370 | ND | 158 | 784 |
| | 10% | 659 | ND | 475 | 605 |
| | 1% | 272 | ND | 154 | 674 |
| | 0.1% | 352 | ND | 139 | 590 |
| PMA 10 ng/ml + Calo | 0% | 1661 | ND | < | 1301 |
| | 10% | 949 | ND | < | 1444 |

TABLE 5-continued

| | % Combined Extracts | IL-2 pg/ml | IL-4 pg/ml | IL-10 pg/ml | IFN-γ pg/ml |
|---|---|---|---|---|---|
| 1 µg/ml | 1% | 1323 | ND | < | 1275 |
| | 0.1% | 1153 | ND | < | 1408 |

As can be seen in Table 5, presence of the herbal extract composition comprising extract of ARUM, extract of POMEGRANATE, extract of TEA and extract of HIBISCUS induces production of considerable amounts of interleukin 10 (IL-10) and γ-interferon (IFN-γ) over the levels secreted in wells without the herbal extracts. Interleukin 2 (IL-2 is detectable in wells where the combined extracts are present in 10% concentration. No toxicity was observed in the cell cultures at 10% concentration of the combined extracts as measured by trypan blue. These results indicate that the combined extracts of ARUM, POMEGRANATE, TEA and HIBISCUS boost or stimulate cytokine production in vitro in PMBCs from normal persons. These results further demonstrate that the herbal extract composition of the invention is a useful source or candidate for potential immune disorder therapies and treatments.

EXAMPLE 6

In Vitro Inhibition of gp120 Binding to MT-4 Cells Measured with OKT4A Monoclonal Antibody.

The effect of the herbal extract composition comprising extract of ARUM, extract of POMEGRANATE, extract of TEA and extract of HIBISCUS ("combined extracts") on the binding of rpg 120 to MT-4 as checked with OKT-4A monoclonal antibodies (mAb) was determined using the method described by J. Neyts, D. Reymen, D. Letourneur, J. Jozefonvicz, D. Schols, J. Este, G. Andrei, P. McKenna, M. Witvrouw, S. Ikeda, J. Clements and E. De Clercq in *Differential Antiviral Activity of Derivatized Dextrans*, Biochem. Pharmacol., Vol. 50, p. 743–751 (1995), the contents of which are incorporated herein by reference. The HIV coat protein gp1 20, which binds to the OKT-4A epitope, blocks competitive binding of the OKT-4A mAb. The combined extracts of ARUM, POMEGRANATE, TEA and HIBISCUS blocks binding of gp120 as shown in Table 6.

TABLE 6

| Sample Wells | OKT-4A Mab Binding (Relative No. Cells) |
|---|---|
| Negative Controls | 4 |
| Positive Controls | 600 |
| gp120 | 7 |
| 50% Combined Extracts | 150 |
| 25% Combined Extracts | 100 |
| 12.5% Combined Extracts | 90 |
| 6.25% Combined Extracts | 80 |
| 3.13% Combined Extracts | 30 |
| 1.57% Combined Extracts | 10 |
| 0.79% Combined Extracts | 8 |

As can be seen from Table 6, where increasing amounts of herbal extract composition comprising extract of ARUM, extract of POMEGRANATE, extract of TEA and extract of HIBISCUS result in increasing inhibition of binding of gp120 to MT-4 cells. These results demonstrate that the herbal extract composition comprising extract of ARUM, extract of POMEGRANATE, extract of TEA and extract of HIBISCUS is a useful source or candidate for potential in vivo anti-HIV therapies and treatments in infected hosts.

EXAMPLE 7

In Vitro Inhibition of gp120 Binding to MT-4 Cells Measured with Anti-gp120 Monoclonal Antibody.

The effect of the herbal extract composition comprising extract of ARUM, extract of POMEGRANATE, extract of TEA and extract of HIBISCUS ("combined extracts") on the binding of rpg120 to MT-4 as checked with anti-gp120 monoclonal antibodies (mAb) was determined using the method described by D. Schols, M. Baba, R. Pauwels, and E. De Clercq in *Flow Cytometric Method To Demonstrate Whether Anti-HIV-1 Agents Inhibit Virion Binding To T4+ Cells*, the contents of which are incorporated herein by reference. The combined extracts of ARUM, POMEGRANATE, TEA and HIBISCUS blocks the binding of gp120 as shown in Table 7.

TABLE 7

| Sample Wells | Anti-gp120 mAb Binding (Relative No. Cells) |
| --- | --- |
| Negative Controls | 4 |
| Positive Controls | 90 |
| 50% Combined Extracts | 60 |
| 10% Combined Extracts | 70 |
| 2% Combined Extracts | 40 |
| 0.4% Combined Extracts | 80 |
| Dextran Sulfate, 25 μg/ml (Positive Control) | 50 |

As can be seen from Table, the herbal extract composition comprising extract of ARUM, extract of POMEGRANATE, extract of TEA and extract of HIBISCUS inhibits binding of gp120 to MT-4 cells. These results demonstrate that the herbal extract composition comprising extract of ARUM, extract of POMEGRANATE, extract of TEA and extract of HIBISCUS is a useful source or candidate for potential in vivo anti-HIV therapies and treatments in infected hosts.

EXAMPLE 8

Chemical Analysis of Combined Extracts

Conventional analytical techniques were used to investigate the chemical composition of the herbal extract composition comprising extract of ARUM, extract of POMEGRANATE, extract of TEA and extract of HIBISCUS, for various vitamins, fats, dyes, proteins, minerals and other compounds. These analytical results are summarized in Table 8.

TABLE 8

| Analysis Subject | Method | Result |
| --- | --- | --- |
| Fat content, total | Lyophilization | 3.698 g/100 ml |
| Fat content, residue | Lyophilization | 3.50 g/100 ml |
| Fat content, residue | Rotational Evaporation | 4.83 g/100 ml |
| Insolubles | Gravimetric | 0.198 g/100 ml |
| Ash content, wet 105° C. | Gravimetric | 1.4 g/100 ml |
| pH value, undiluted | Electrometric | 5.20 |
| pH value, 1:10/water | Electrometric | 5.47 |
| Carbohydrates, total | Photometric | 20% of dry matter |
| Macromolecules | Gel Permeation Chromatography, grav. | 15% of dry matter |
| Proteins, total | Photometric | 2.8 mg/100 ml |
| Polysaccharides, total | Photometric | 7.8% of dry matter |
| Polysaccharides, insol. | Photometric | 0.1% of dry matter |
| Polysaccharides, soluble | Photometric | 7.5% of dry matter |
| Nucleic acids, total | Photometric | 53.7 mg/100 ml |
| RNA | Photometric | 28.4 mg/100 ml |
| DNA | Photometric | 25.2 mg/100 ml |
| Polyphenols | Photometric | <2 mg/100 ml |
| Lipids, total | TLC | <0.1% |
| Na | Flame coloring | +++ |
| K | Flame coloring, $KClO_4$ | + |
| Mg | Titanium yellow | ++ |
| Ca | Oxalate | ++ |
| Zn | Dithizon | + |
| Cu | Methocuproin | + |
| Phosphate | Ammonium Molybdate | +++ |
| Immunoglobulin A (IgA) | BIA with protein G chip, AC with jacaline sepharose | Not provable |
| Immunoglobulin G (IgA) | BIA with immobilized protein A | + |
| Immunoglobulin M (IgM) | BIA with immobilized protein B | Not provable |
| Immunoglobulin E (IgE) | Anti-Igs on test plate | Note provable |
| Adenosine | TLC | ++ |
| Guanosine | TLC | + |
| Thymidine | TLC | ++ |
| N,N dimethylguanosine | TLC | Not provable |
| Adenine | TLC | + |
| Guanine | TLC | + |
| Cytosine | TLC | + |
| Thymine | TLC | + |
| Stearic acid | TLC | <1 mg/ml |
| Interleukin 4 (IL-4) | ELISA | 34 pg/ml (NWG 50 pg/ml |
| Interleukin 5 (IL-5) | ELISA | 332 pg/ml (NWG 50 pg/ml |
| Interleukin 6 (IL-6) | ELISA | 69 pg/ml (NWG 30 pg/ml |
| Interleukin 10 (IL-10) | ELISA | 44 pg/ml (NWG 50 pg/ml |
| Interleukin 12 (IL-12) | ELISA | 1095 pg/ml (NWG 1000 pg/ml |
| γ-interferon (IFN-γ) | ELISA | 29 pg/ml (NWG 50 pg/ml |
| Tumor Necrosis Factor α (TNFα) | ELISA | 5.7 pg/ml (NWG 3 pg/ml |
| Red dye | UV/Vis | 0.7% of dry material |
| Green dye | UV/Vis | 15.7% of dry material |
| Yellow dye | UV/Vis | <0.2% of dry material |
| Blue dye | UV/Vis | <0.1% of dry material |
| Vitamin C | TLC, photometric | 3 mg/100 ml |
| Vitamin E | TLC | + |
| Vitamin K | TLC | + |
| Vitamin D2 | TLC | + |
| Vitamin D3 | TLC | + |
| Endotoxins | LAL test | 14 IU |

As can be seen from the results in Table 8, the herbal extract composition comprising extract of ARUM, extract of POMEGRANATE, extract of TEA and extract of HIBISCUS include numerous essential vitamins, including Vitamin C, Vitamin E, Vitamin K, Vitamin D2, Vitamin D3, as well as various essential minerals other beneficial materials, and thus provides a useful and nutritional diet supplement when ingested orally.

The analytical results shown in Table 7 also indicate that various cytokines or cytokine-like proteins are present in the herbal extract composition comprising extract of ARUM, extract of POMEGRANATE, extract of TEA and extract of HIBISCUS. Particularly, detectable amounts of IL-4, IL-5, IL6, IL-10, IL-12, IFN-γ, and TNFα are present in the combined extracts of ARUM, POMEGRANATE, TEA and HIBISCUS. Additionally, traces of IgG or an immunoglobulin-like protein appear to be present in the herbal extract composition comprising extract of ARUM, extract of POMEGRANATE, extract of TEA and extract of HIBISCUS. The presence of human IL-4, IL-5, IL6, IL-10, IL-12, IFN-γ, TNFα and IgG is somewhat inconsistent with the vegetable origin of the herbal extract composition. However, plant antiviral factors (AVF) are known which have a close sequence homology to human β-interferon (IFNβ), and which are believed to exert antiviral activity in a manner similar to that of human interferons. Thus, the positive results for IL-4, IL-5, IL6, IL-1, IL-12, IFN-γ, TNFα and IgG described above may be due to interleukin-like proteins, interferon-like proteins, TNF-like proteins, and immunoglobulin-like proteins which are present in the herbal extract composition comprising extract of ARUM, extract of POMEGRANATE, extract of TEA and extract of HIBISCUS. Thus, the term "herbal extract composition comprising extract of ARUM, extract of POMEGRANATE, extract of TEA and extract of HIBISCUS" as used herein should be understood as also including or comprising IL-4, IL-5, IL6, IL-10, IL-12, IFN-γ, TNFα and IgG, as well as interleukin-like proteins, interferon-like proteins, TNF-like proteins, and immunoglobulin-like proteins.

DISCUSSION

The above in vitro experiments and resulting data demonstrate that the herbal extract composition of the invention is a useful potential source or candidate for immunity boosting therapies and treatments for humans and animals suffering from disorders, diseases infections or conditions, including immunosuppressed conditions due to leukemia, renal failure, various cancers and tumors, viral infections, bacterial infections, and parasitic infections. The precise chemical composition(s) and pharmacological mechanism(s) which result in the in vitro blast transformation stimulation and cytokine production have not been elucidated. The herbal extract composition of the invention may contain a single pharmacological active ingredient, component or agent acting alone, or a combination of such ingredients, components or agents, and/or biological metabolites or derivatives thereof acting separately or synergistically. In vivo therapies and treatments using the herbal extract composition of the invention will likely be based on orally ingested dosages of the herbal extract composition in liquid or solid form. Rectal, parenteral, intravenous, topical, aerosol inhalation or subcutaceous routes for in vivo administering of the herbal extract composition of the invention are also possible. The herbal extract composition may also be administered in vivo in admixture or combination with appropriate excipients, carriers, antiviral agents, immune modulators, chemotherapeutic agents, antibodies, or combinations thereof. Pharmacological preparations of the invention may be dosage unit forms such as tablets, capsules, suppositories, ampoules or metered liquid or aerosol dosages.

Presently, it is believed that the pharmacologically active component or components of the invention are present in ARUM and/or POMEGRANATE. Initial experiments indicate that extract of ARUM alone, extract of POMEGRANATE alone, and combined extracts of ARUM and POMEGRANATE exhibit some immuno-boosting effects. However, the preferred embodiment of the invention comprises combined extracts of ARUM and POMEGRANATE as well as TEA and HIBISCUS. It is believed that TEA and HIBISCUS provide other additional components or agents which act as excipients or carriers or which otherwise have a synergistic effect together with the components provided by ARUM and POMEGRANATE. Additionally, the preferred method of making the herbal extract composition comprising extract of ARUM, extract of POMEGRANATE, extract of TEA and extract of HIBISCUS, wherein the combined extracts are heated together in stages as described Example 1, is believed to be more advantageous than the mere mixing or combining of extract of ARUM, extract of POMEGRANATE, extract of TEA and extract of HIBISCUS together without additional heating.

The above in vitro experiments and resulting data also demonstrate that the herbal extract composition of the invention is a useful potential source or candidate for anti-HIV and other antiviral therapies and treatments for humans and animals suffering from HIV, other viral infections, or complications or disorders associated with such viral infections. The herbal extract of the invention may potentially inhibit or prevent infection of cells by a variety of different viruses, including, but not limited to, herpes simplex viruses, human papilloma viruses (HPV), vaccinia viruses, vesicular stomatitis viruses, coxsackie viruses, syncyctial viruses, cytomegalovirus, and varicella zoster viruses. The anti-HIV activity of the herbal extract composition of the invention may contain a single pharmacological active ingredient, component or agent acting alone, or a combination of such ingredients, components or agents, and/or biological metabolites or derivatives thereof. In vivo therapies and treatments using the herbal extract composition of the invention for anti-HIV and antiviral treatments will likely be based on orally ingested or topically applied dosages of the herbal extract composition in liquid or solid form. Rectal, parenteral, intravenous, aerosol inhalation or subcutaceous routes for in vivo administering of the herbal extract composition of the invention are also possible. As for treatment of immunosuppresive treatments, the herbal extract composition may also be administered in vivo for antiviral treatments in admixture or combination with appropriate excipients, carriers, antiviral agents, immune modulators, chemotherapeutic agents, antibodies, antiviral agents or combinations thereof. Pharmacological preparations of the invention may be dosage unit forms such as tablets, capsules, suppositories, lotions, ampoules or metered liquid or aerosol dosages.

Accordingly, it will be seen that this invention provides an herbal extract composition which provides a nutritious supplement which stimulates in vitro cell mediated immunity, which stimulates in vitro lymphocyte blastogenesis, which stimulates in vitro cytokine production by lymphocytes, which inhibits in vitro HIV infection, and which provides a potential candidate for treatments and therapies for boosting or stimulating the immune esponse in humans and animals. Although the description above contains many specificities, these should not be construed as limiting the scope of the invention but as merely providing an illustration of the presently preferred embodiment of the invention. Thus the scope of this invention should be determined by the appended claims and their legal equivalents.

What is claimed is:

1. An herbal extract composition for stimulating cell mediated immunity comprising a mixture of an aqueous extract of ARUM leaves or roots, an aqueous extract of POMEGRANATE FRUIT PEEL, an aqueous extract of TEA LEAF, and an aqueous extract of HIBISCUS FLOWERS, wherein said composition contains about equal portions of said extracts in amounts effective to stimulate cell mediated immunity.

2. A method of preparing an herbal extract composition for stimulating cell mediated immunity, comprising the steps of:

(a) preparing an extract of ARUM LEAVES AND/OR ROOTS by boiling dried, finely crushed ARUM LEAVES &/OR ROOTS in water;

(b) preparing an extract of POMEGRANATE FRUIT PEEL by boiling dried, finely crushed POMEGRANATE FRUIT PEEL in water;

(c) preparing an extract of TEA LEAVES by boiling dried, finely crushed TEA LEAVES in water;

(d) preparing an extract of HIBISCUS FLOWERS by boiling dried, finely crushed HIBISCUS FLOWERS in water; and (e) combining and heating said extracts obtained from steps (a) through (d) to obtain an herbal extract composition containing a mixture of said extracts;

(f) whereby said composition obtained from step (e) contains about equal portions of said extracts.

3. A method of stimulating in vitro cell mediated immunity comprising contacting cells with an effective amount of a composition consisting essentially of an aqueous extract of ARUM LEAVES AND/OR ROOTS, an aqueous extract of POMEGRANATE FRUIT PEEL, an aqueous extract of TEA LEAVES, and an aqueous extract of HIBISCUS FLOWERS, wherein said composition contains approximately equal portions of said extracts.

4. The method of claim 3, wherein said cells comprise cells from normal patients.

5. The method of claim 3, wherein said cells comprise cells from patients having leukemia.

6. The method of claim 3, wherein said cells comprise cells from patients having renal failure.

* * * * *